United States Patent [19]

Rovelli et al.

[11] Patent Number: 5,081,013

[45] Date of Patent: Jan. 14, 1992

[54] IMMUNODIAGNOSTIC DEVICE AND METHOD

[75] Inventors: Cesare Rovelli; Domenico Brustolin; Paola Piro, all of Milan, Italy

[73] Assignee: Boehringer Biochemia Robin S.p.A., Milan, Italy

[21] Appl. No.: 231,016

[22] Filed: Aug. 11, 1988

[30] Foreign Application Priority Data

Aug. 14, 1987 [IT] Italy .................... 21658 A/87

[51] Int. Cl.$^5$ .................. G01N 33/543; G01N 33/558
[52] U.S. Cl. ..................... 435/7.92; 422/56; 422/60; 435/7.93; 435/7.95; 435/967; 435/970; 436/514; 436/518; 436/810
[58] Field of Search ............ 435/7, 805, 7.92, 7.93, 435/7.95, 967, 970; 436/514, 518, 530, 809, 810; 422/56, 57, 60

[56] References Cited

U.S. PATENT DOCUMENTS 4,446,232  5/1984  Liotta ...................... 436/514
4,690,907  9/1987  Hibino et al. .............. 436/514
4,861,711  8/1989  Friesen et al. ............. 436/514
4,900,663  2/1990  Wie et al. ................. 435/7

FOREIGN PATENT DOCUMENTS 0284232  9/1988  European Pat. Off. .
8604683  8/1986  World Int. Prop. O. .
8906791  7/1989  World Int. Prop. O. .

*Primary Examiner*—David A. Saunders
*Attorney, Agent, or Firm*—Armstrong, Nikaido, Marmelstein, Kubovcik & Murray

[57] ABSTRACT

A method of, and a device for performing immune enzyme analyses are described, wherein positiveness or negativeness of an analysis is evaluated by colorimetric comparison of a chromogen zone of determination with a chromogen zone of reference, on which zones reactions are occurring, or not, between the chromogen system and an enzyme conjugated with immunoreactive substances which will reach said zones in different quantities when a sample to be analyzed contains the analyte of which it is desired to acertain the presence.

5 Claims, 23 Drawing Sheets

IMMUNODIAGNOSTIC DEVICE AND METHOD

This invention relates to a device immunodiagnostic assays, more specifically to a device for performing analyses of the immune enzyme type, and to a method utilizing the device for analyzing biological samples by affinity chromatography and colorimetrically reading the results by comparing at least two zones in the device of the invention where a colorimetric detection reaction takes place.

PCT/EP86/00055, in the name of the applicant, discloses an immune enzyme diagnostic device and a method based on the affinity and/or capillarity chromatography.

According to said Patent Application, a biological sample containing a substance capable of being analyzed by immunodiagnostic techniques is caused to pass through a support that is divided into zones on which the following substances are conveniently adsorbed in proper sequences:
(a) an enzyme-labelled, immunoreactive substance;
(b) an immobilized immunoreactive substance (i.e. capable of fixing the substance (a) and/or the product of immune reaction between the analyte and the substance (a)); and finally,
(c) a chromogen substance.

By the term "immunoreactive" it is meant the capability of giving rise to reactions of the antigen-antibody or anti-antibody type with the analyte.

Also provided in said device are further zones containing substances able to eliminate indesirable interferences and the document discloses the various possible configurations for the support according to whether the analyte is an antigen or an antibody. In any case, according to the method and device known, evaluation of the results is made by reading on the zone (c) an absolute colorimetric value that may possibly be compared with a preprinted colorimetric scale obtained from previously made calibrations, with the same support, by using analyte samples of known titers.

Limitations to this reading system are, in the most frequent case of visual evaluation, the "background" phenomenon typical of immunologic reactions, and the individual responsiveness to, and capability of distinguishing color variations, which latter may, inter alia, be influenced by a number of factors (e.g. climatic conditions, ageing or imperfect conservation of a support, not homogeneous times of contact, etc. . . .). Thus, it is apparent that even the preprinted scale fails to help in completely solving the problem and this problem may be a very critical one in the case of a marginally positive analysis when very light variations in color are involved.

The above disadvantages are removed by this invention which provides devices and methods wherein reading is made by comparing the color developed in a chromogen zone (c) with the color simultaneously developed in a reference zone associated with said chromogen zone (c).

The relative evaluation of one color with respect to the other, both of which colors are originated from reactions occurring simultaneously under the same conditions on the same sample, is certainly more trustworthy and permits doubts and uncertainties, that are especially undesirable when using the device at one's private house, to be overcome.

The method utilizing the device according to the invention, comprises the step of simultaneously contacting a sample to be analyzed with a support that is substantially divided into two portions, namely a determination portion and a reference portion, each of these support portions being in turn divided into a number of zones on which there are adsorbed in a proper sequence:
(a) an enzyme-labelled substance that is immunoreactive towards, or competitive with an analyte;
(b) an immobilized substance being immunoreactive towards the substance (a) or the analyte, or towards the immune complex of analyte and substance (a); and
(c) a chromogen system;

said reference portion having at least one other zone than has the determination portion, on which other zone a substance immunoreactive towards the analyte has been irreversibly adsorbed, or on which other zone a labelled substance immunoreactive in respect of the analyte is reversibly adsorbed, in such a manner that, in the presence of an analyte, the colorimetric reaction on the chromogen zone of the reference portion takes place to a different extent from the colorimetric reaction on the chromogen zone of the determination portion.

For convenience in performing reading and comparison, the two chromogen zones are made to be adjacent so that evaluation of differences in color may be easier.

An enzyme-labelled immunoreactive substance is an enzyme-labelled antibody when the analyte is an antigen, or it is an enzyme-labelled anti-antibody when the analyte is an antibody. On the other hand, a substance competitive with the analyte is represented by the same analyte (antigen or antibody) that has been marked with enzyme.

The immobilized immunoreactive substance in zone b is the same analyte (antigen, antibody, anti-antibody) that has been immobilized in a proper quantity on one zone of the device.

Finally, a chromogen system consists of substances capable of producing a colorimetric reaction when in contact with the enzyme by which the substance immunoreactive with the analyte is marked.

These systems, based on the use of marking enzymes such as peroxidase, glucoseoxidase, $\beta$-galactosidase, alkaline phosphatase, etc. are known and have been employed long since.

The device of the invention preferably also includes zones, in both the reference portion and determination portion thereof, on which there are adsorbed substances that are able to eliminate any possible, undesired interferences.

The support device according to the invention may be in the form of a strip, ribbon, film, tube, specimen, bottle, swab, etc. The determination and reference portions may be disposed side-by-side on a common support or they may be separate portions and used independently of one another. The various components may be adsorbed or directly immobilized on the material of the device or on suitable solid supports placed in the inside of the device or fixed on the surfaces thereof in the form of gel, powder, granules, microspheres, spheres, etc.

The materials of the device and the solid supports at the various reactive zones may be the same or different; representative examples of suitable materials and supports include glass, silica derivatives, paper or cellulose derivatives, metals, polymers such as polyvinyl chloride, polystyrene, polybutadiene, nylon, polyacrylamides methacrylates, etc., polysaccharides, or polyols, starch, stabilized human or animal red blood cells, inorganic substances such as $BaSO_4$, $TiO_2$, kaolin, infusioral earth, diatomaceous earth, etc.

The bond immobilizing the antibodies or antigens on said materials may be obtained by physical or chemical processes (formation of ester or amide bonds, etc.), as disclosed in U.S. Pat. No. 4,003,988 and reported in the literature (see: B. K. Van Weemen and A. H. A. Schuurs, Febs Letters—vol. 15, n. 3 - June 1971 -pp 232–5; P. Leinikki and Suvi Passila, J. Clin. Path., 1976, 29—pages 1.116-20; B. R. Brodeur, F. E. Ashton and B. B. Diena, The Journal of Medical Microbiology—vol. 15, N. 1 - 1981 pages 1-9; A. Voller 1; D. E. Dibwell 2, A. Bartlett 2, D. G. Fleck 3, M. Perkins 3 and B. Oladehin 3, J. Clin. Path., 1976, 29, pages 150-3; Howard H. Weetall, Immobilized Enzymes, Antigens, Antibodies, and Peptides—vol. 1).

The adsorption binding of the not immobilized components can, on the other hand, take place by known techniques, for example by simple inhibition of materials of suitable porosity, as is well known in the affinity chromatography field.

Both the immobilized and the enzyme-labelled antibodies as used according to the invention, may be poly- or monoclonal, in toto, or in fragments thereof, for example, Fab' and F(ab')$_2$, possibly in mixture, and they may be specific for one or more active sites of the antigen.

The enzyme-labelling of antigens or antibodies may be carried out by known techniques such as those described in "Enzyme Immunoassay", E. Ishikawa, T. Kawai, K. Miyai, Igaku-Shoin- Tokyo-New York (1981), by using any enzyme capable of giving rise to a chromogenic reaction in respect of a substrate, and as for example peroxidase, alkaline phosphatase, $\beta$-galactosidase or the like. These enzymes may for example be conjugated by means of glutaraldehyde, dimaleimide and its esters, by techniques as described in "Enzyme Immunoassay", pages 54 to 113.

Both the antibodies and antigens can be fixed to a support without restrictions as to quantity, which may in any case vary from 1 to 10 mg/cm$^2$ according to the desired type of analysis. The only condition is that the immobilized component and the enzyme-labelled component should be present in proper quantities (e.g., at least stoichiometrically equivalent quantities). As referred to above, a quantitative evaluation is possible by evaluating the intensity of a color developing either arbitrarily or by means of a proper reflection reader.

Finally, the interference suppressing zone, when provided, may simply be a material having chromatographic support property, which material may carry substances previously adsorbed thereon which are able to suppress any compound interfering with the recognition reaction. Thus, ion-exchange resins may be employed for sequestering heavy metals, immobilized enzymes for degrading urea or other metabolites, antiprotein antibodies for eliminating albumin, antibodies specific for molecules similar to the antigen to be determined, etc.

The method and device of the invention provide means for the rapid and accurate determination of a great number of different clinical parameters including, for example, hormones of peptide nature, such as hCG, LH, somatotropin FSH, ACTH, LPH, MSH, beta-endorphins, enkephalins, prolactin, vasopressin, oxytocin, and the like. Steroid hormones, immunoglobulins. Bence-Jones proteins, 1-$\alpha$-antichymotrypsin, 1-$\alpha$-antitrypsin, 1-$\alpha$-microglobulin, 2-$\beta$-microglobulin, haptoglobin, ferritin, transferrin, antithrombin III, myoglobin, myosin light chain, cryoglobulins, prealbumin, calmodulin, albumin, fibronectin, specific glycoprotein of pregnancy (SPI), retinol-binding proteins (RBP). Enzymes such as GOT, GPT, ALP, ACP, LDH, gamma-GT , creatine kinase, LAP, amylase, MAO, 5'-nucleotidase, OCT, lipase, pancreatin, plasminogen activator, catalase, lipoprotein lipase, phospholipase, DNase, RNase, transferase, pepsin, trypsinogen, chymotrypsin, enterokinase, aminopeptidase, enolase, tyrosine hydroxylase, peroxidase, dopamine, $\beta$-hydrolase, dopa decarboxylase. Carbohydrates including acid mucopolysaccharides, inulin, gangliosides, mucopolysaccharides. Lipids, e.g. cholesterol, lipoproteins, triglycerides, apolipoproteins, phospholipids, etc. Vitamins including vitamin A, D, E, K, B-6, B-12, thiamine, ubiquinone, riboflavins, nicotinic acid, folic acid, ascorbic acid, inositol. Clotting factors including the fibronigen, FDP, plasminogen, factor VIII, factor IX, factor XI, factor XII, factor III, factor V, factor VII, factor X, prothrombin, beta-thromboglobulin, 2-betamacroglobulin, thrombocyte factor 4, thrombocyte membrane proteins. Catecholamine-type hymor secretion substances, metanephrine, normetanephrine, homovallic acid, 3-4-dihydroxyphenylalanine, 3-4-dihydroxy acetic acid, 3-methoxy-4-hydroxyphenylethylene glycol, dopamine-beta-hydroxylase, aldosterone, 11-deoxycorticosterone, corticosterone, 18-hydroxycorticosterone, cortisol, 11-deoxycortisol, 11-hydroxycorticosteroid, androstenedione testosterone, 5-$\alpha$-dihydrotestosterone, estrone, estradiol, estriol, estetrol, catechol, estrodiene, progesterone, pregnanediol, 17-hydroxyprogesterone, pregnanetriol, placental prolactin (mammogen).

Substances derived from digestive and pancreatic secretion such as, for example, insulin, proinsulin, C-peptide, pancreatic glucagon, gastrin, secretin, CCK-PZ, motilin, enteroglycagon, pancreatic peptides, somatostatin, P substances, neurotensin. Antigens used in syphilis and immunoserologic tests of pathogenic microorganisms. Virus, for example, antimycoplasma antibodies, rickettsia, antistreptolysin 0, antistreptokinase, antideoxyribonuclease, herpes simplex virus, herpes zoster, cytomegalovirus, EBV, anti-EBV antibodies, adenovirus, influenza virus A, B, C, parainfluenza virus, virus RS, mumps virus, measles virus, rubella virus, Japanese encephalitis virus, poliovirus, hepatitis virus A, B, S, E, C, nonA, nonB, rhinovirus, coronavirus, mumps, coxsackie virus, chlamydia, rota virus. Autoantibodies, for example, antinuclear antibodies, antiDNA antibodies, antiENA antibodies, rheumatoid factor, antiglobulins, LE cells, antimitochondria, smooth anti-muscle antibody, striated anti-muscle antibody, cardiac anti-muscle antibody, antiinsulin antibodies, insulin antireceptor antibodies, acetylcholine antireceptor antibodies. Cellular substances including the Clq, Clr, Cls, C2, C3, C4, C5, C6, C7, C8, C9 complement factors, tumor markers as, for example, CEA, AFB, BFB, polyamines, CRP, immunoacetic proteins, POA. Molecules of the phenobarbitol type, primidone, phenytoin, carbamazepin, valproic acid, lidocaine, digoxin, digitoxin, theophylline, deisopyramide, mexiretina, propranolol, diuretics, synthetic steroids, chloramphenicol, aminoglycosides, antitubercular agents, methotrexate, opiates, methadone, barbital, amphetamines, cocaine metabolites, benzodiazepine metabolites, propoxyphene, cannabinoids. Antitoxoplasma gondi antibodies. Moreover, the same supports can have a number of enzyme-labelled antigens and/or antibodies fixed to them with the corresponding antibodies and/or antigens being immobilized thereon, so as to permit a number of clinical parameters to be determined simultaneously, owing to the presence, on different zones, of a corresponding number of chromogen substrates which are preferably such as to produce different colors by reaction with different enzyme-labelled complexes.

The invention will now be explained in more details in relation with embodiments thereof, reference being made to the accompanying drawings which show, by way of non restrictive examples, only a few of the possible configurations of the devices according to the invention, and in which:

FIG. 1 shows an embodiment of a device for the determination of an antigen.

FIGS. 2a to 2d schematically show different stages of an analysis carried out by the device in FIG. 1 in the presence of an analyte to be analyzed (positive analysis).

Figures 3A, 3B:
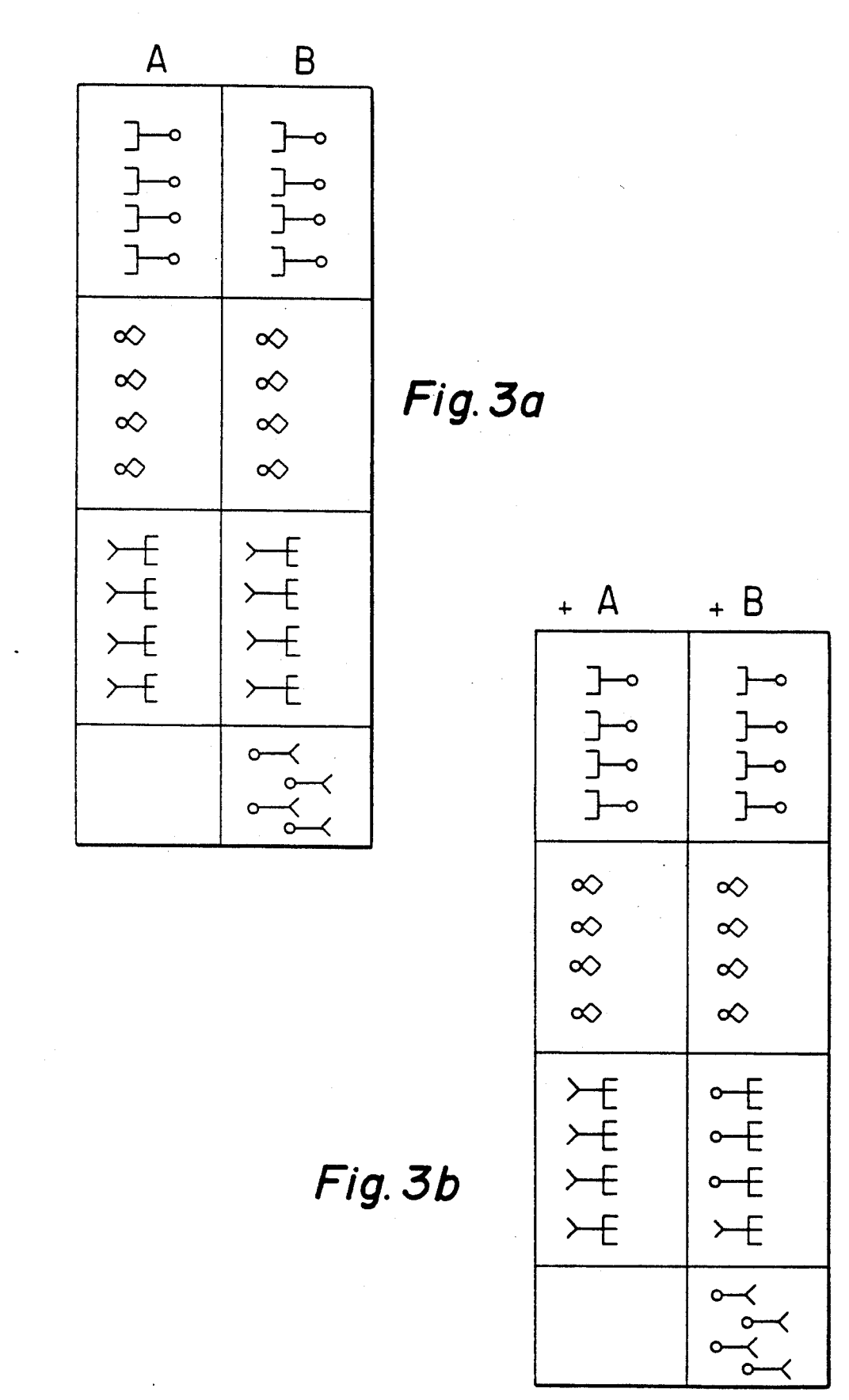

FIGS. 3a to 3d show different stages of an analysis performed by the device in FIG. 1 in the absence of an analyte to be analyzed (negative analysis).

Figure 9:
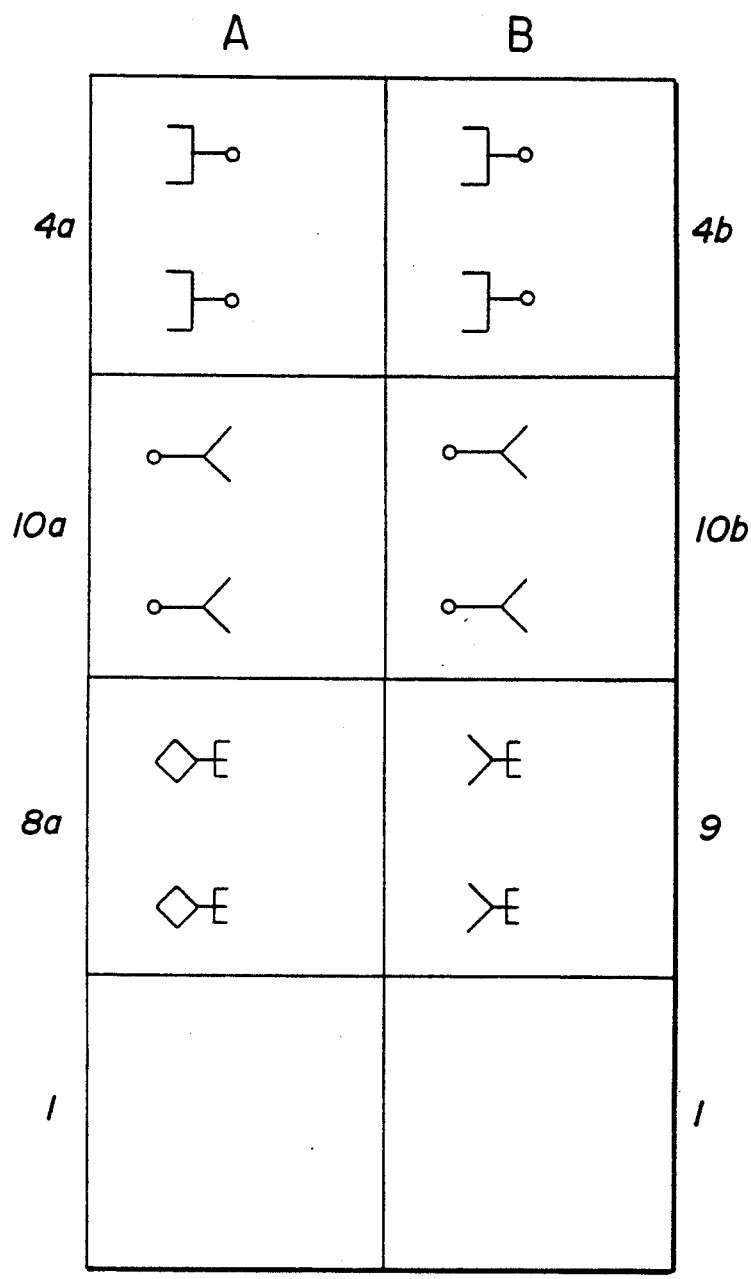
FIG. 9 shows an embodiment of a device for the determination of an antigen, wherein an enzyme-labelled substance is used which is competitive with the antigen.
Figure 10A:
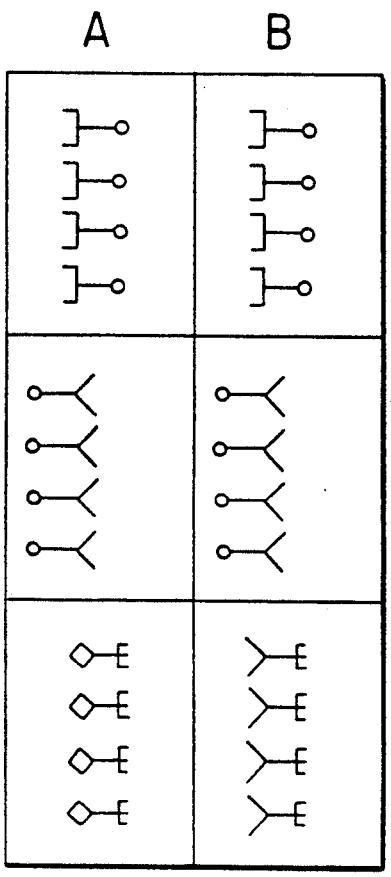
Figure 10A:
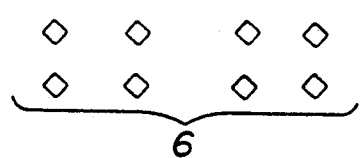
Figure 10B:
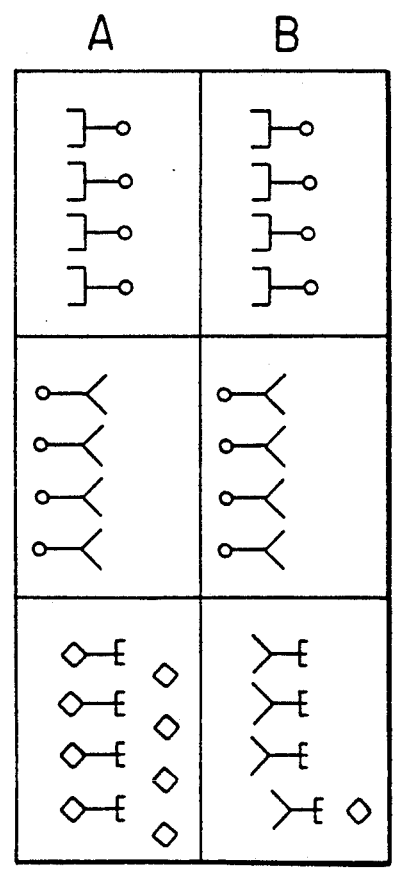
Figure 10C:
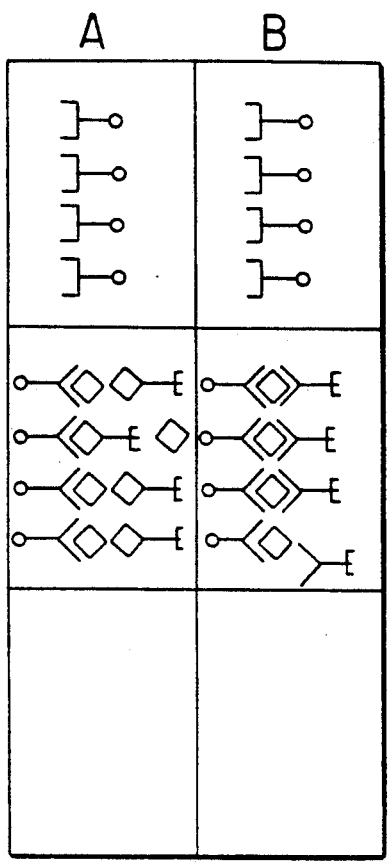
Figure 10D:
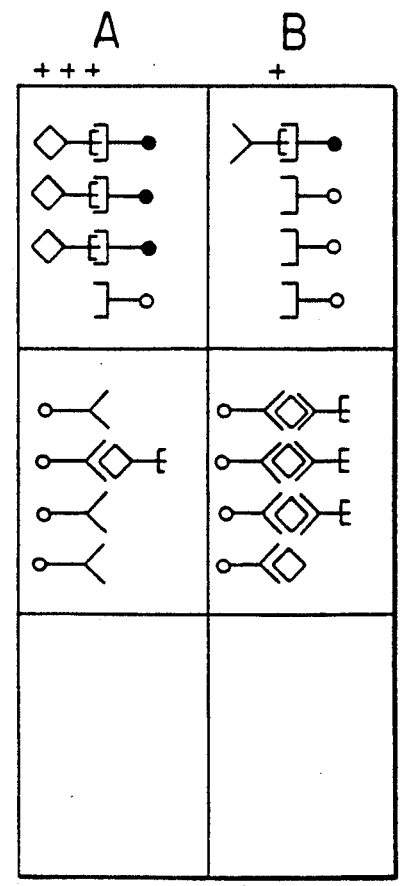
Figure 11A:
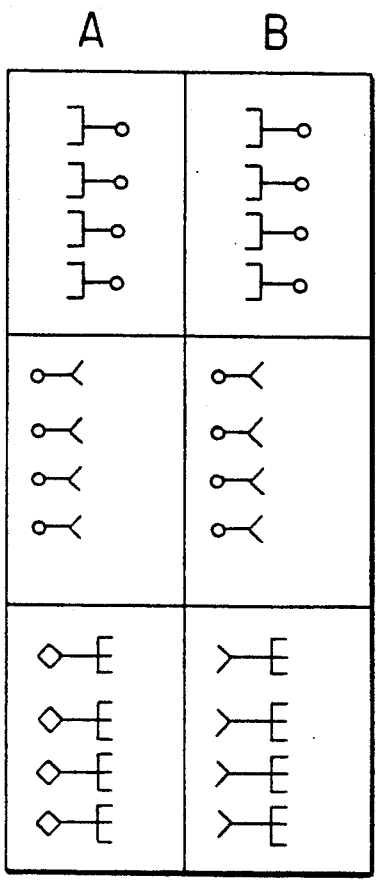
Figure 11B:
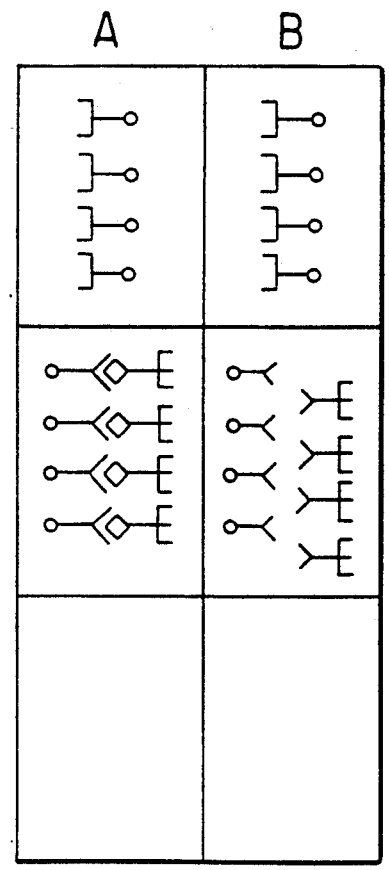
Figure 11C:
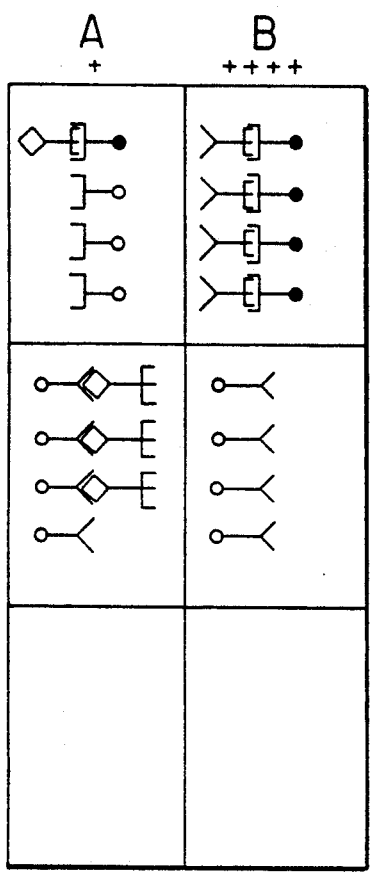
Figure 14A:
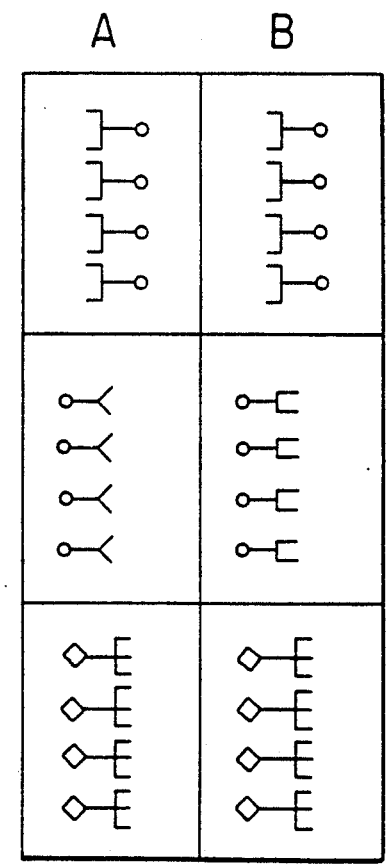

FIGS. 10a to 10d and 11a to 11c schematically show the cases of positive and negative analyses, respectively, utilizing the device in FIG. 9.

Figure 4:
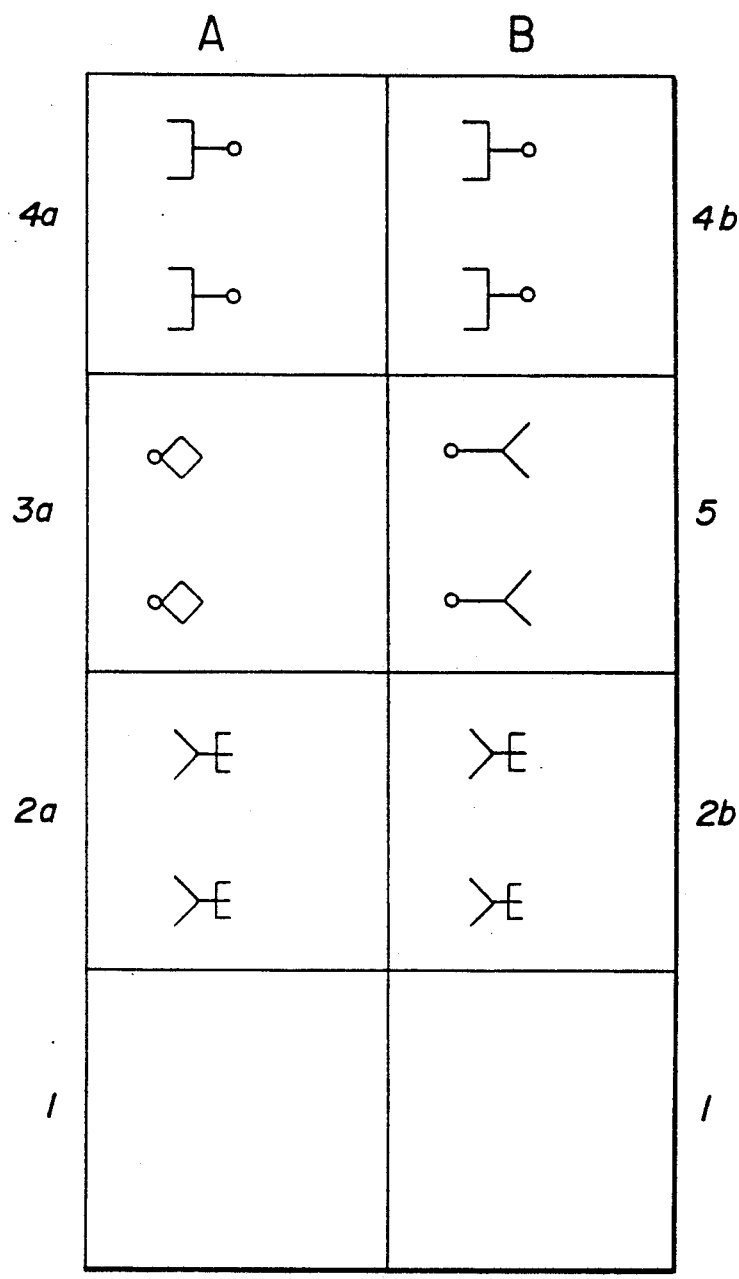
FIG. 4 shows a second embodiment of a device for determining an antigen.
Figure 12:
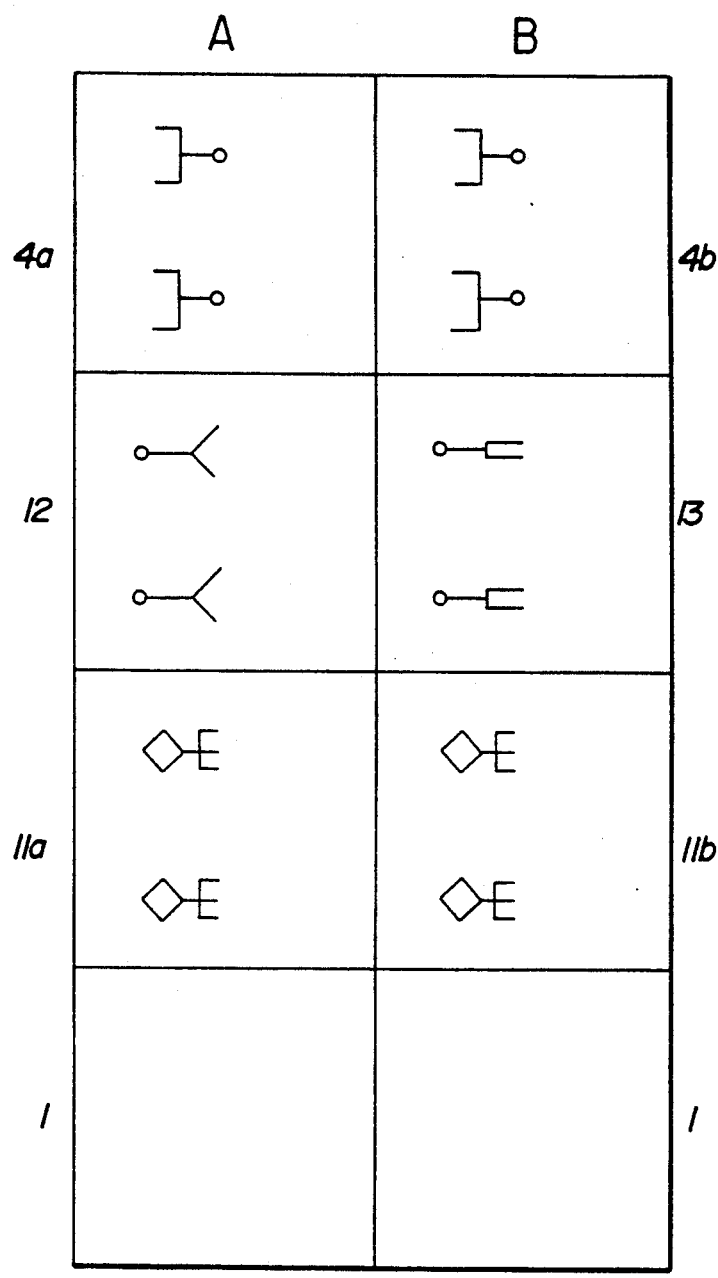
Figure 13A:
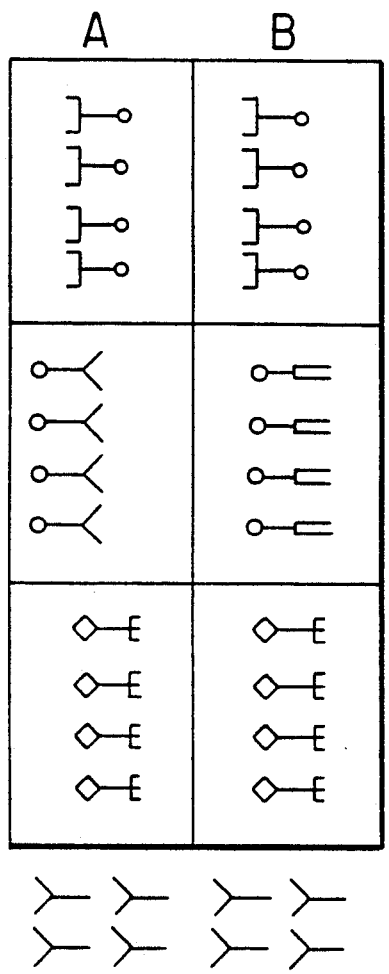
Figure 13A:
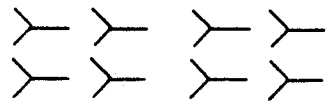
Figure 13B:
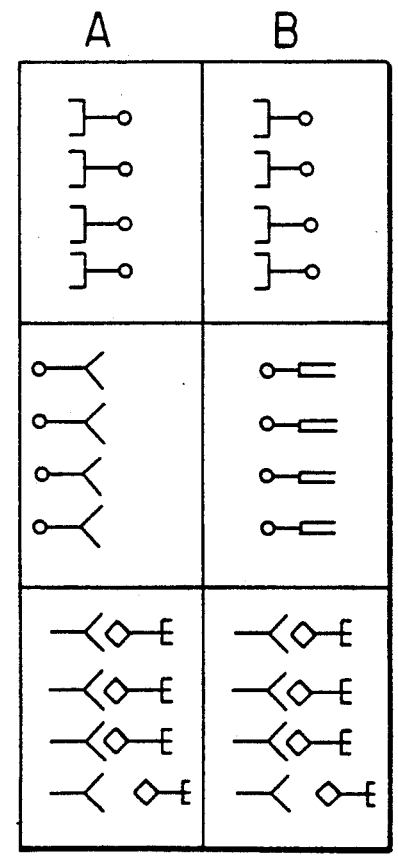
Figure 13C:
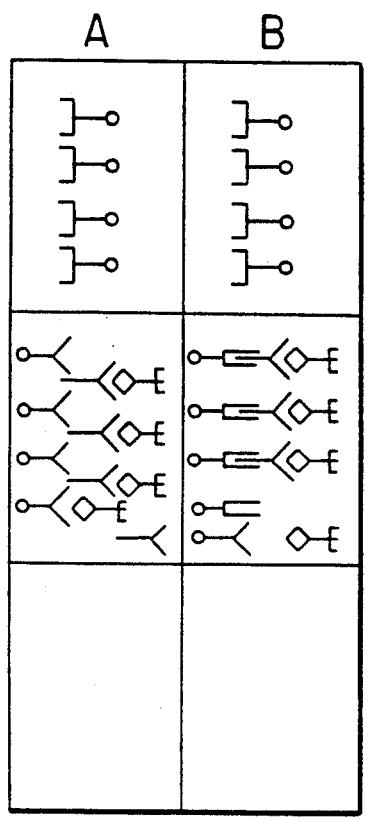
Figure 13D:
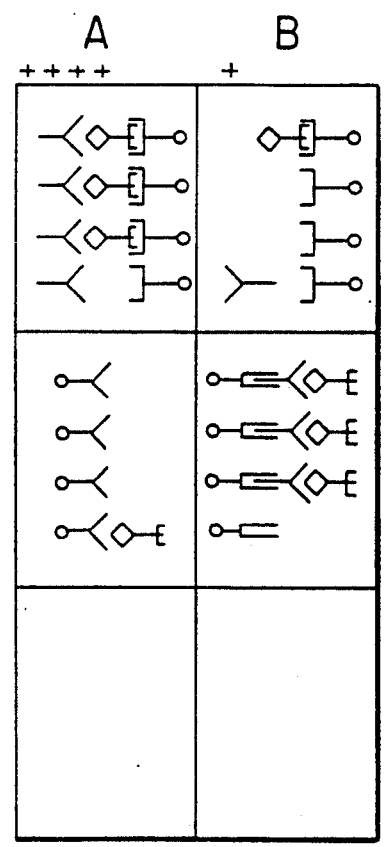
Figure 14B:
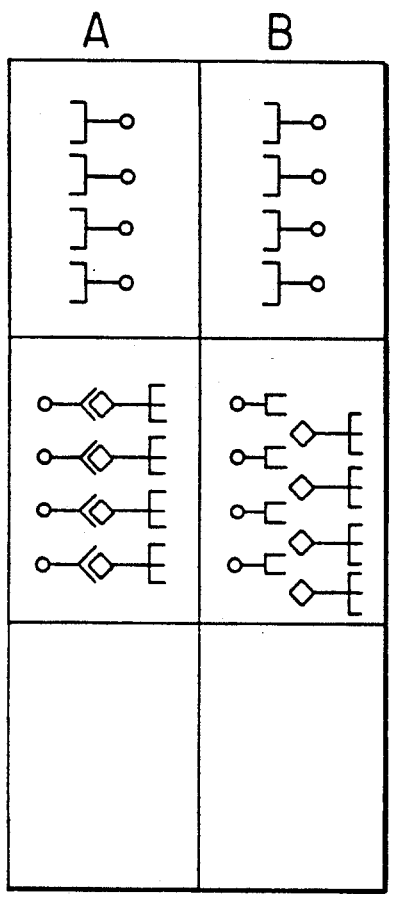
Figure 14C:
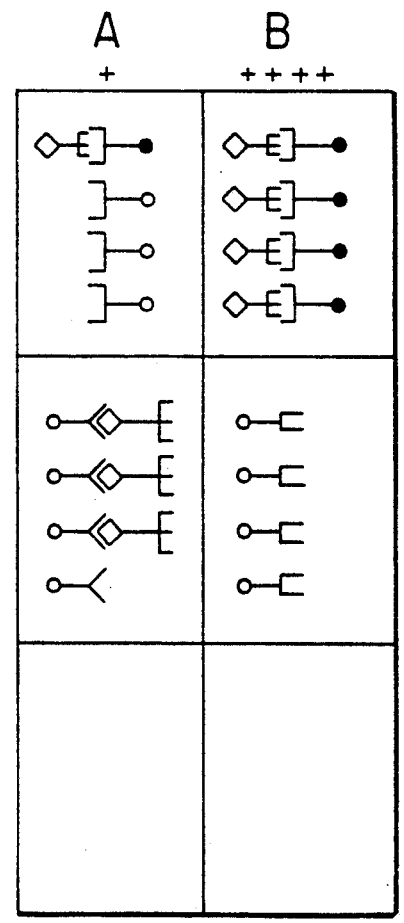

FIG. 12 shows an arrangement of a device for the determination of an antibody which is conceptually similar to that in FIG. 4.

FIGS. 13a to 13d and 14a to 14c respectively show the cases of positive and negative analyses utilizing the device in FIG. 12.

Figure 1:
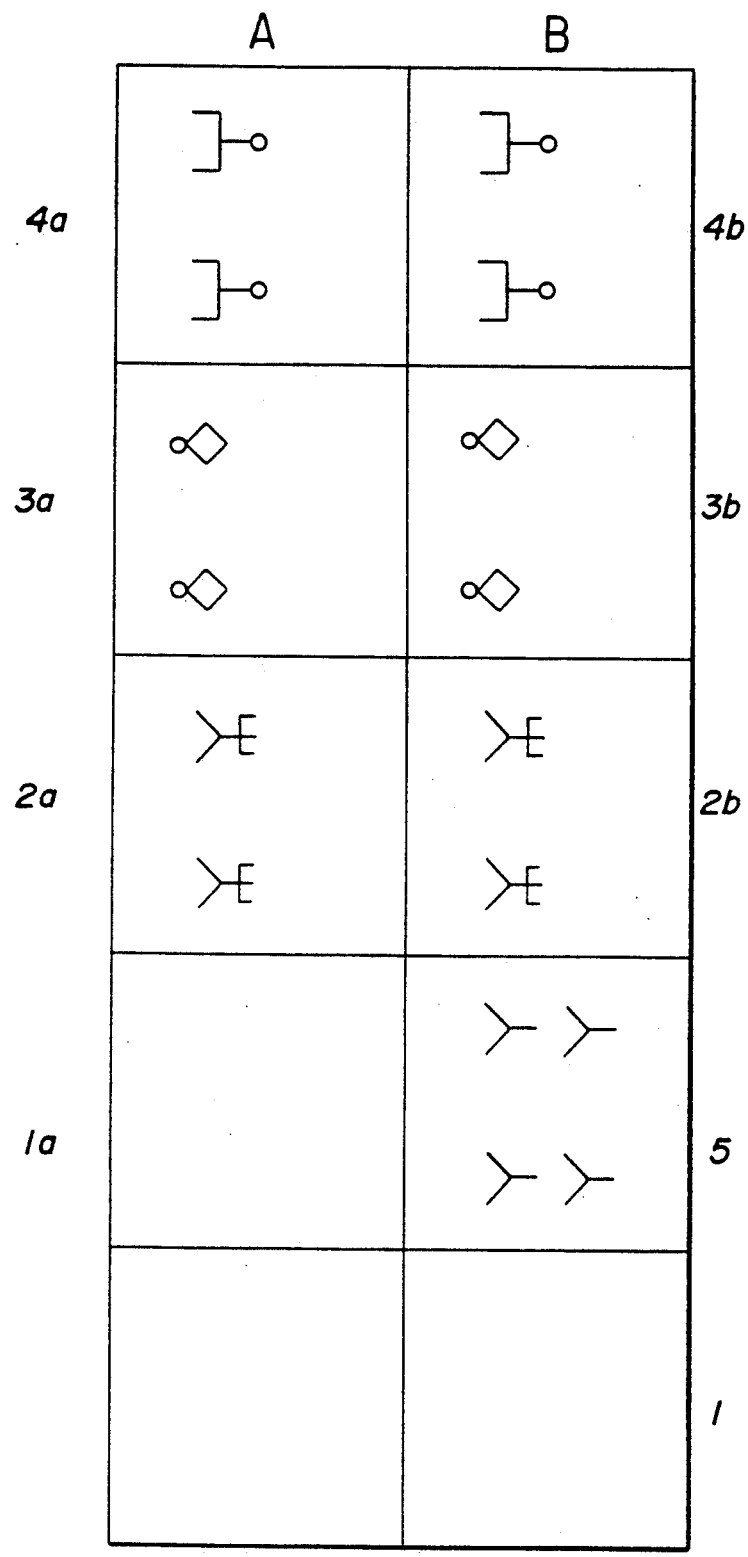
Figure 2A:
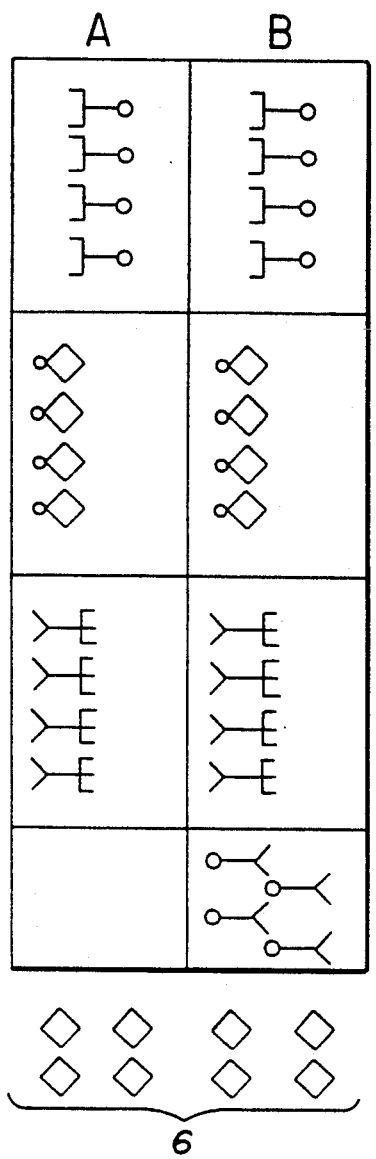
Figure 2B:
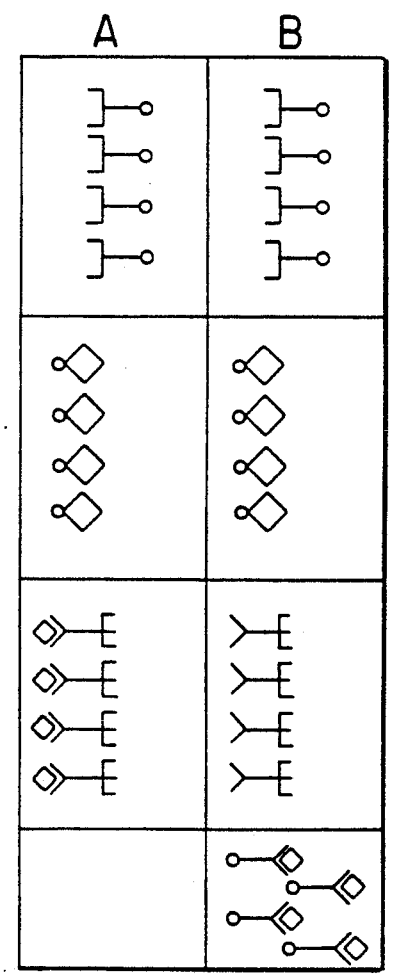
Figure 2C:
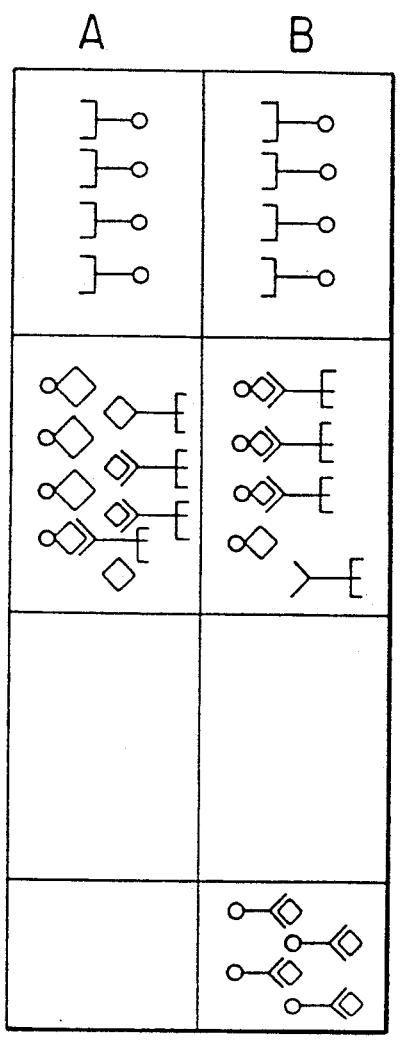
Figure 2D:
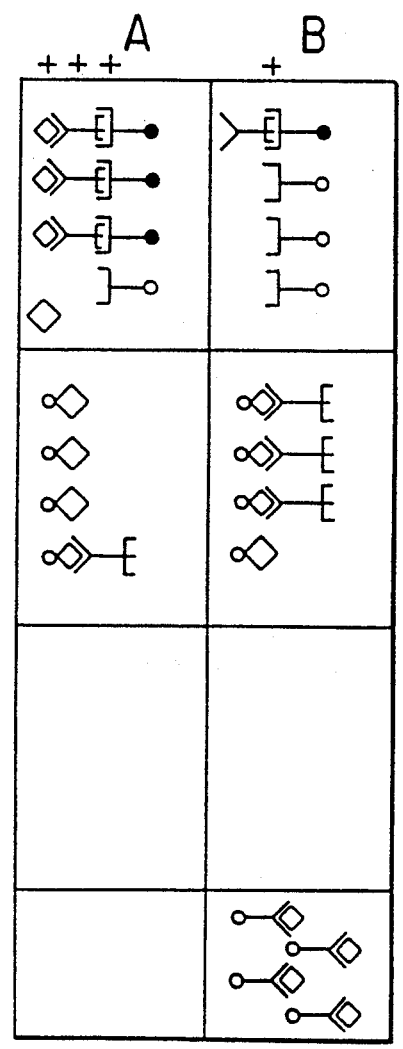
Figure 3C:
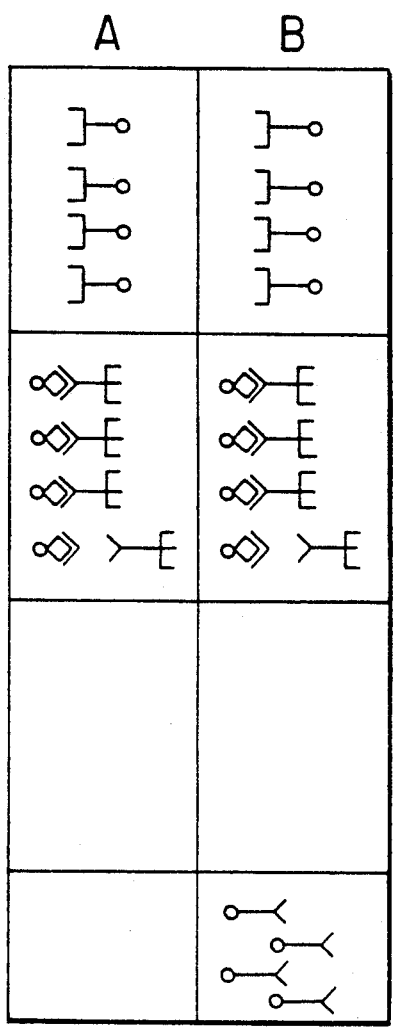
Figure 3D:
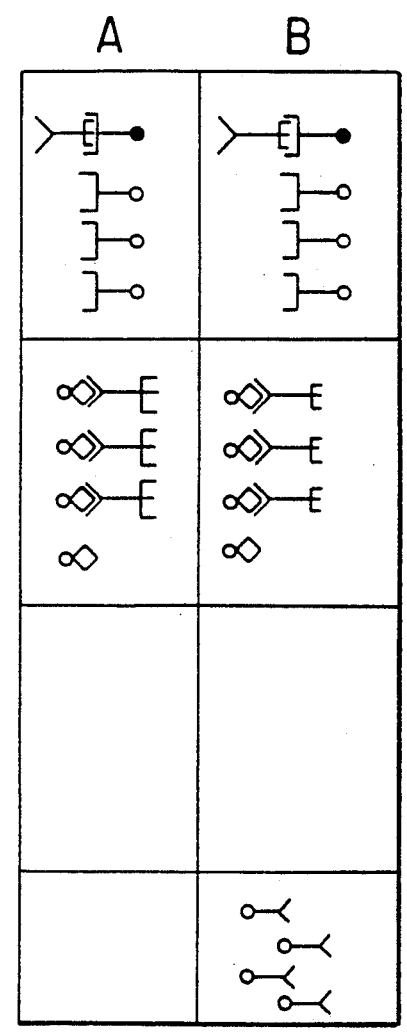

Reference is made now to FIG. 1 where A designates a determination portion and B a reference or comparison portion. In said portions: zone (1) is a first zone intended for eliminating any interference; zone (1a) contains inert material permitting the flow of biological liquid; zones (2a) and (2b) (portions A and B respectively) have enzyme-conjugated antibodies reversibly adsorbed thereon; in a similar way, zones (3a) and (3b) have suitable quantities of antigens, corresponding to the analyte to be analyzed, irreversibly fixed thereto; zones (4a) and (4b) contain a chromogen system.

Provided in the reference portion B is a zone (5) having one or more mono- or polyclonal antibodies irreversibly bonded thereon, directed towards the analyte. In this same zone it is also possible to use substances capable of absorbing and/or completely holding the analyte and such as nitrocellulose, protein A, ion-exchange resins, glass or derivatives thereof, celulose and derivatives thereof.

Referring now to FIGS. 2a–2d, an antigen to be determined, designated by numeral (6), present in a biological sample of interest, will bind to the enzyme-labelled antibodies in the determination portion and to the antibodies immobilized in the reference portion. As the liquid continues to flow by capillarity, gravity, pressure, chromatography, suction or diffusion through the device, the enzyme-labelled antigen-antibody complex in portion A becomes free to reach the chromogen zone while the enzyme-labelled antibody in portion B will remain trapped by the antigen immobilized in zone (3b).

Thus, positivity of the analysis can unequivocally be evaluated because of the developed color in zone (4a) being higher in strength than in zone (4b).

Instead in case of negative sample (FIGS. 3a to 3d), the enzyme-labelled antibodies in zones (2a) and (2b) will simultaneously migrate towards the zones 4a and 4b, which are, however, attained by no quantity of enzyme-labelled antibody or a negligible amount thereof, said antibody remaining for the most part fixed to the zones 3a and 3b. Thus, the zones 4a and 4b will retain their original color or they will both develop a light coloration of the same low intensity (background). The above-described device can be easily adapted for the determination of an antibody by using an enzyme-labelled antigen in zones (2a) and (2b), an immobilized antibody in zones (3a) and (3b) and an immobilized antigen in zone 5.

Alternatively, anti-antibodies specific for antigen-antibody complexes, may be used in zones (3a) and (3b): in this case the zones (2a) and (2b) will in turn be divided into two zones respectively containing the enzyme-labelled antigen and the corresponding antibody. FIG. 4 shows an alternative embodiment for the determination of an antigen (or possibly an antibody, mutatis mutandis). In FIG. 4, the same reference letters and numerals as in FIG. 1 correspond to the same meanings as explained in relation to FIG. 1.

In case of positive analysis (presence of antigen 6 in the sample) as shown in FIGS. 5a to 5d, the enzyme-labelled antigen (analyte)-antibody complex is free to reach the chromogen zone in portion A whereas it remains firmly held in zone 5 of portion B. The zone 4a will be higher in color strength than zone 4b which latter remains colorless or takes on a light coloration due to background.

Figure 6A:
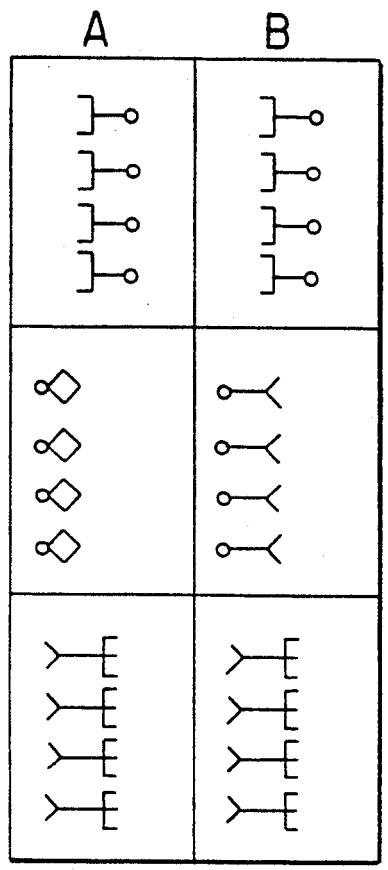
FIGS. 6a to 6c show the analysis with no analyte being present (negative analysis).
Figure 6B:
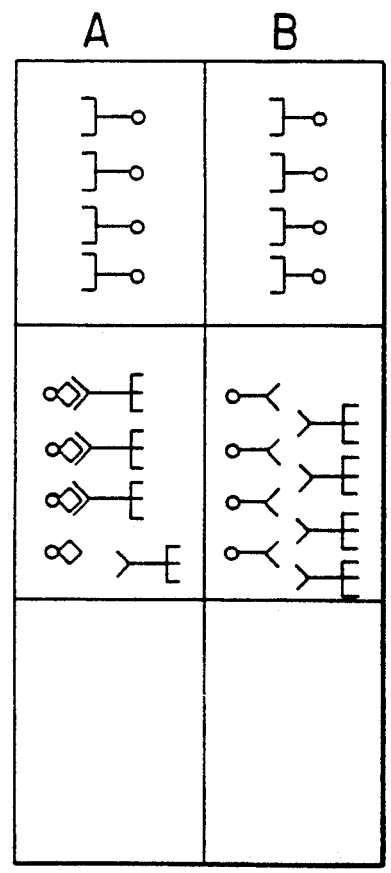

In case of negative analysis (FIGS. 6a–6c), only the enzyme-labelled antibody in portion B will be able to reach the chromogen zone, whereas the enzyme-labelled antibody in portion A will remain firmly held by the immobilized antigen in (3a). Thus, a coloration higher in strength is obtained in reference zone (4b) than in zone (4a).

Figure 8E:
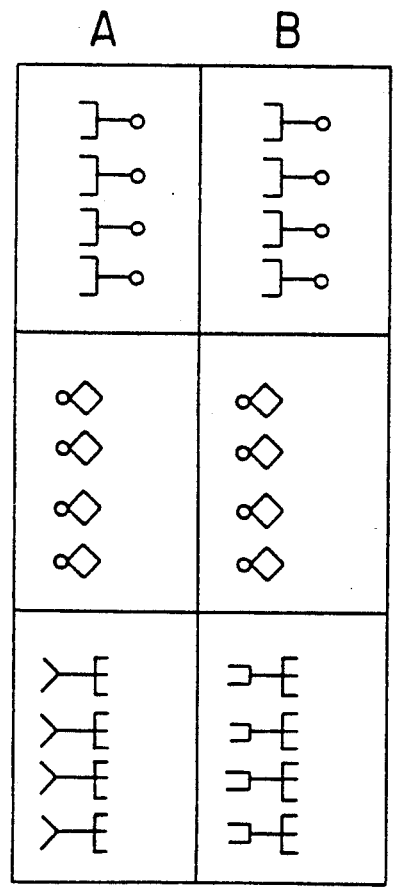
FIGS. 8a to 8d and 8e to 8g are equivalent to FIGS. 2a to 2d and 5a to 5d and show the various steps of a positive analysis (FIGS. 8a to 8d) and of a negative analysis (FIGS. 8e to 8g).
Figure 7:
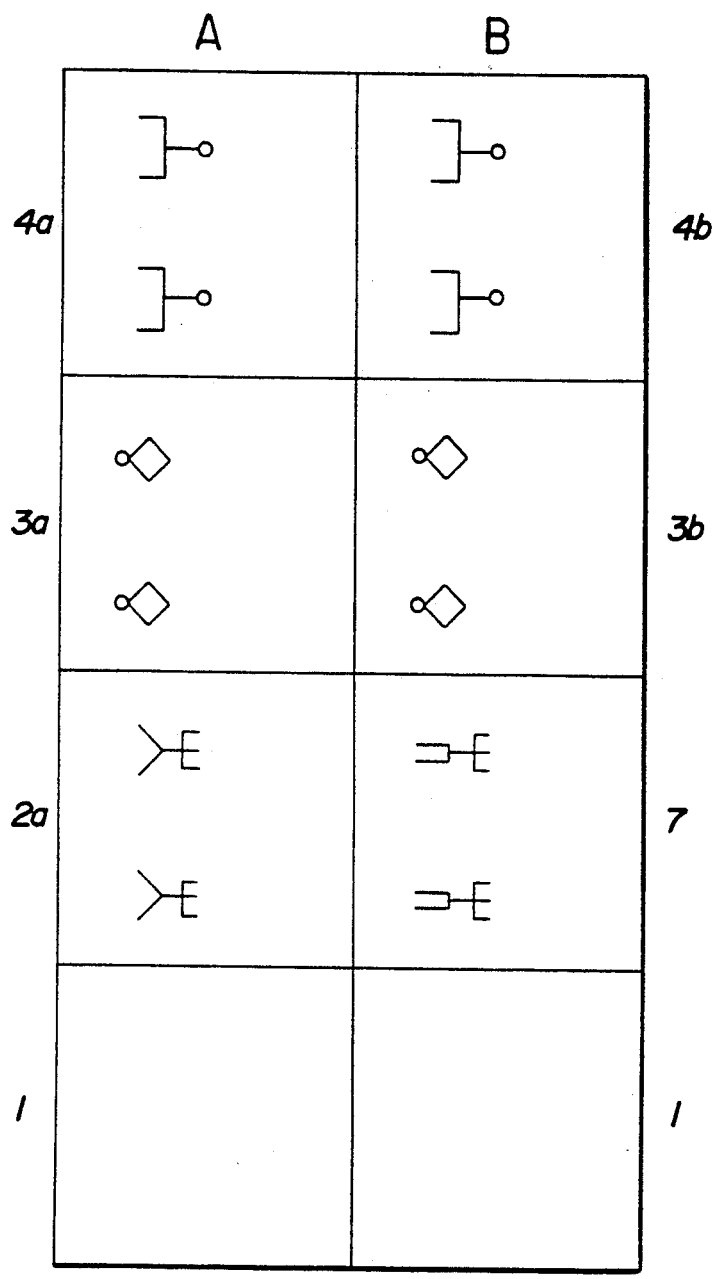
FIG. 7 shows an embodiment of a device for the determination of an antibody.
Figure 8A:
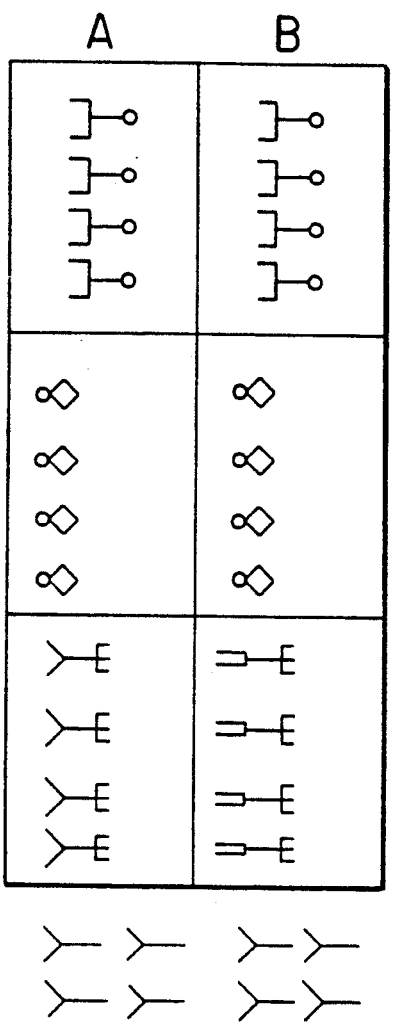
Figure 8B:
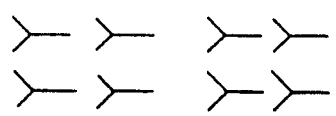
Figure 8B:
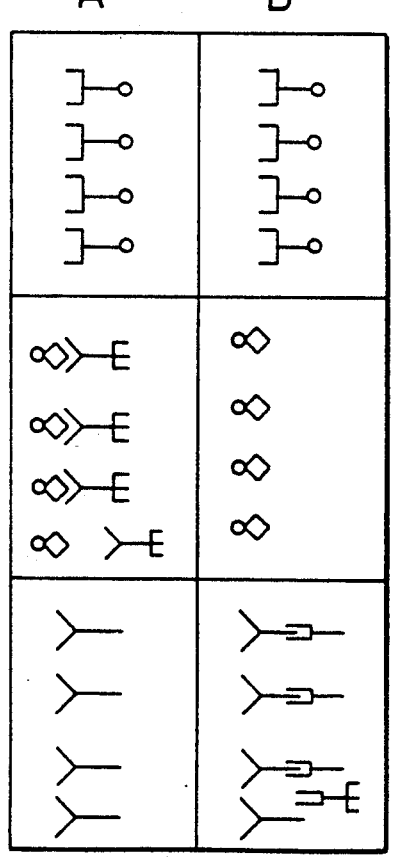
Figure 8C:
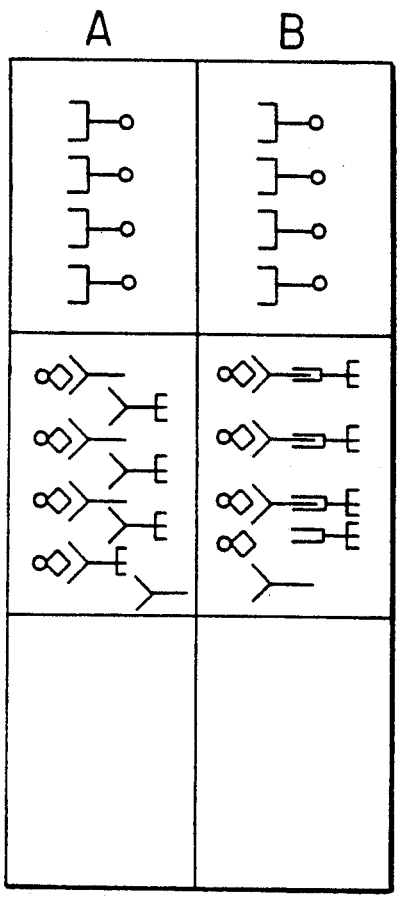
Figure 8D:
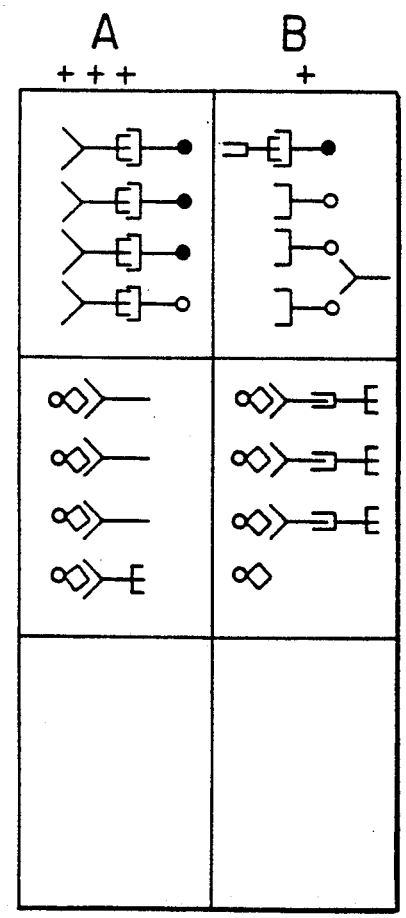
Figure 8F:
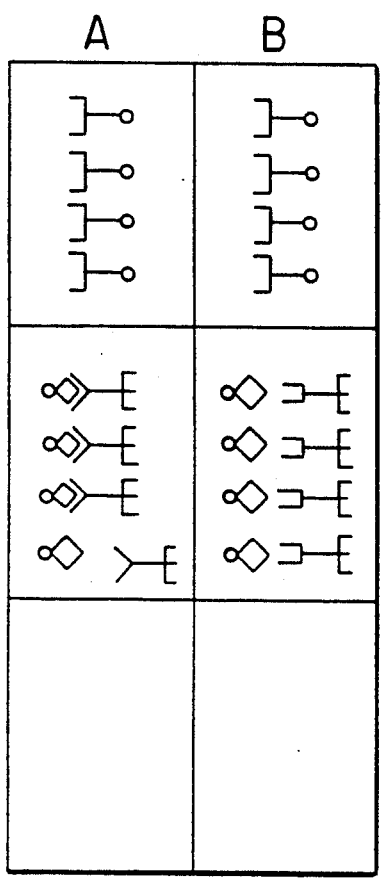
Figure 8G:
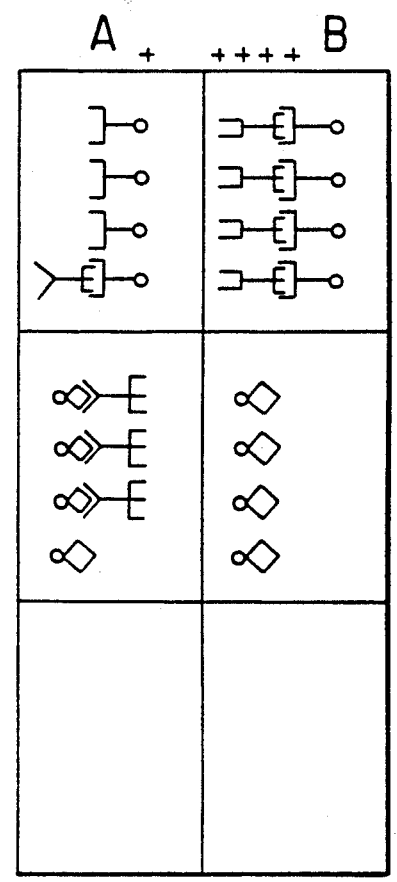

FIG. 7, where, again, the same reference letters and numerals correspond to the same meanings as already explained above, relates to a device for the determination of an antibody, in which an enzyme-conjugated anti-antibody is adsorbed on zone 7 in a reversible manner. With this embodiment shown, in case of positive analysis (FIGS. 8a–8c) the enzyme-labelled antibody in zone 2a, which has initially been fixed by the immobilized antigen in zone (3a) (FIG. 8b), is competitively set free by the antibody present in the sample and, thus, caused to migrate towards the chromogen zone. In the comparison portion B the immunocomplex that is being formed in zone 7 between the antibody to be analyzed and the enzyme-labelled anti-antibody, remains, on the contrary, firmly held by the immobilized antigen (3b) (FIG. 8c) and is unable to reach the detection zone (4b). In case of negative analysis (FIGS. 8e–8g), the enzyme-labelled antibody, in portion A, is moved to zone 3a to be firmly held there by the immobilized antigen, and a weak coloration is developed in the detection zone 4a due to background. In portion B, due to the zone 3b not being able to firmly hold the enzyme-labelled anti-antibody, this latter is moved to the detection zone which will, thus, be more strongly colored than zone 4a.

FIG. 9 shows that, in the determination portion A, antigens corresponding to the analyte, conjugated with enzyme, are reversibly adsorbed on zone 8a while antibodies specific for the analyte are irreversibly adsorbed on zone 10a. In comparison portion B, the zone 9 comprises, reversibly adsorbed thereon, antibodies specific for the analyte, conjugated with enzyme. The zone 10b is identical with zone 10a. In case of positive analysis (FIGS. 10a–10d) the analyte 6 competitively displaces the conjugated antigen away from the antibodies immobilized in 10a (FIG. 10c), thereby to permit a marked coloration to develop in zone 4a whereas only the coloration due to background will develop in zone 4b, owing to the conjugated analyte-antibody immunocomplex remaining fixedly retained by the antibodies immobilized in zone 10b.

In case of negative analysis (figures 11a–11c) a reverse situation will occur, with the zone 4b being more highly colored than the zone 4a: in the absence of an analyte capable displacing the conjugated antigen away form 10a, the antigen bound enzyme fails to reach (except for a minimum part, if any) the chromogen zone. On the contrary, the enzyme-conjugated antibody in portion B is free to reach the chromogen zone. The embodiment in figure 12 finally corresponds to that already shown in FIG. 4 for the determination of an antigen. Therefore, the enzyme-conjugated antigens in zones 11a and 11b, specific for the antibodies to be determined, take the places of the enzymeconjugated antibodies in zones 2a and 2b of FIG. 4, while the immobilized antibody 12 and the immobilized anti-antibody 13 take the places of the antigen immobilized in 3a and the antibody immobilized in 5 FIG. 4, respectively.

Figure 5A:
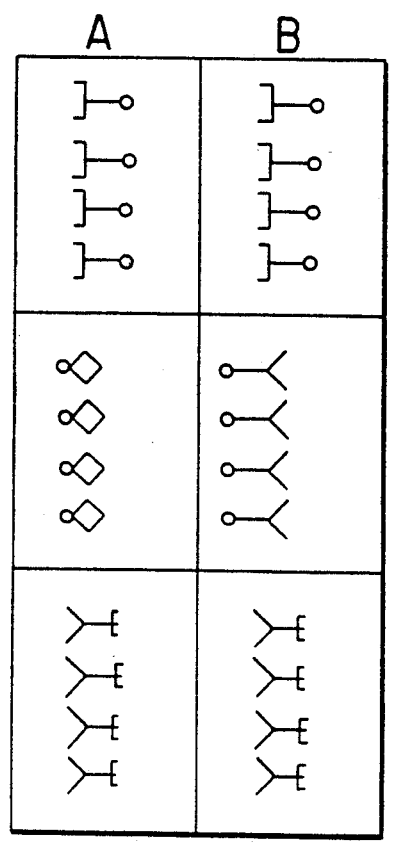
FIGS. 5a to 5d show, in various stages, an analysis by the device in FIG. 4, the analyte to be analyzed being present.
Figure 5A:
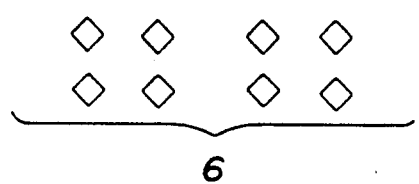
Figure 5B:
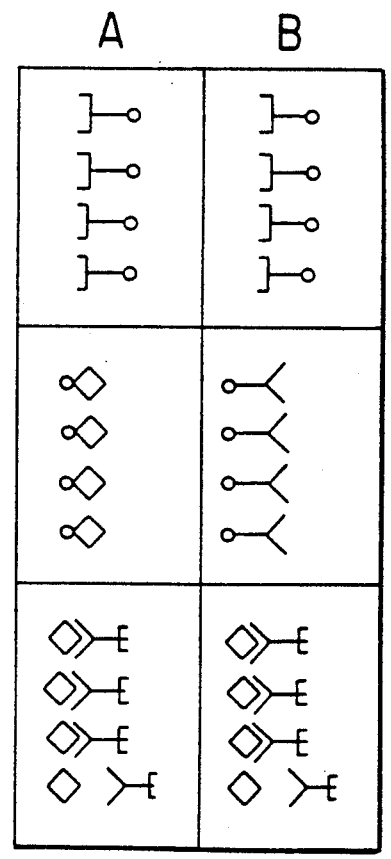
Figure 5C:
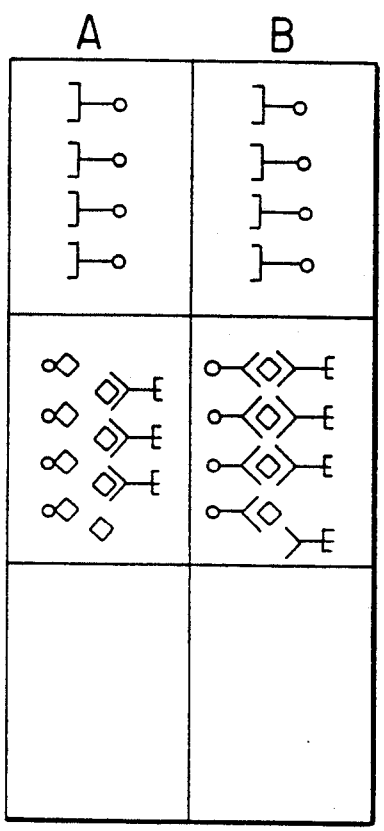
Figure 5D:
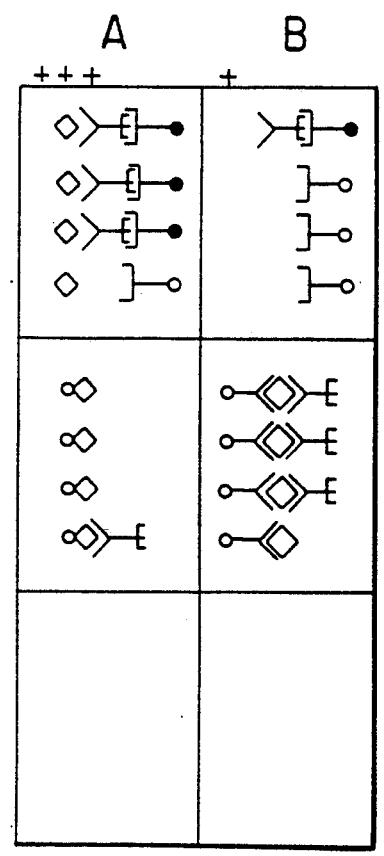
Figure 6C:
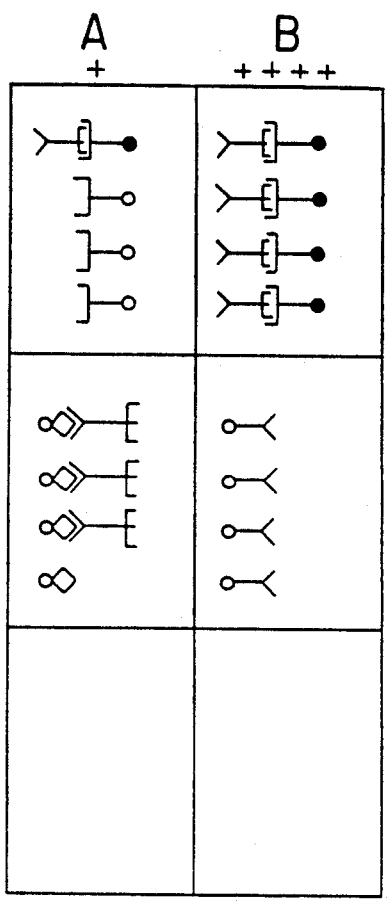

Thus, with the device in FIG. 12 (and related FIGS. 13a–14c), the positive and negative cases are in all respects comparable with those already described in relation to FIGS. 5a and 6c.

It should be apparent that the determination and reference, or comparison, portions in all the devices of the invention are assigned arbitrarily and a same portion may indifferently serve either for reference or for determination purposes.

The following examples are to illustrate more specifically the invention and not to be constructed as limiting the scope thereof.

EXAMPLE 1

Determination of antigen (hCG)

a) Preparation of hCG immobilized on cellulose—Determination portion.

100 g of fiber cellulose is treated with a 50 U/ml hCG solution in phosphate buffer, at pH 7.2, 37° C. for one night. The coated cellulose is washed 5 times with the same buffer then dried 10 hours at 37° C.

b) Preparation of anti-hCG immobilized on cellulose—Reference portion.

100 g of cellulose is treated with 10 mg/l purified rabbit anti-hCG in phosphate buffer, pH 7.2, at room temperature for one night with stirring. The product is washed 3 times with the same buffer, filtered on porous glass membranes, then dried at 37° C. for 10 hours.

c) Preparation of peroxidase-labelled anti-hCG—Determination and reference portions.

10 ml of rabbit anti-hCG is precipitated 3 times by 18% anhydrous sodium sulfate, recovering after each precipitation from 10 ml distilled water. The product is then dialyzed overnight at +4° C. against phosphate buffer at pH 7.2, 10 mM.

The dialyzed solution is treated with 100 mg of RZ 3.00 peroxidase and 25 mc l of 25% glutaraldehyde for 48 hours at +4° C. The solution is eluted on Sephadex G-150 equilibrated with sodium chlroride 50 mM. The anti-hCG-peroxidase complex can be stored at −25° C.

d) Preparation of the labelled, cellulose-adsorbed antibody—Determination and reference portions.

50 g of cellulose is treated with 5 ml of 1:500 diluted anti-hCG-peroxidase in phosphate buffer, 10 mM, pH 7.2 followed by drying at 37° C. overnight.

e) Preparation of the cellulose-adsorbed chromogen—Determination and reference portions.

50 g of cellulose is treated with 90 mg of tetramethylbenzidine dissolved in 5 ml of DMSO-water.

f) Packing of columns.

Two glass columns (3.5 mm int. diameter, 10 cm long) are packed from bottom to top with the following materials: adsorbed anti-hCG-peroxidase, immobilized hCG (determination portion), immobilized anti-hCG (reference portion), adsorbed chromogen, all prepared as herein above. The glass column is closed at both ends with cotton and suitable porous septa.

g) Performing the analysis.

The above described columns are contacted with urine to be analyzed, which urine will rise in the columns by capillarity; when hCG is present in urine, it will bind to the anti-hCG-peroxidase in the first part of the column; the formed immunocomplex, in continuing its way up, goes past the immobilized hCG contained in the second part of the column and moves up further until reaching the chromogenic substrate in the last part of the column, which substrate will produce, by reaction with the enzyme, a blue color development. In the reference column, the enzyme-conjugated antigen-antibody complex will bind to the irreversibly fixed antibody in the second part (sandwich) of the column, and fail to reach the chromogenic substrate in the last part of the column, except for a small fraction which, owing to reaction balance, may form no sandwich and produce a light coloration (background).

Conversely, with no hCG present in urine, in the determination column, the anti-hCG-peroxidase in the first part of the column, in moving up free, will reach the zone containing the immobilized hCG to be bound to it by immunoreaction; it is possible that, owing to reaction balance, a small fraction of enzyme-conjugated antibody is not retained by the antigen and, thus, enabled to reach the chromogenic substrate to develop a light coloration (background).

In the reference device, the enzyme-conjugated antibody will go past the zone where the anti-hCG antibody is immobilized to reach the chromogen zone to develop intense coloration.

h) Reading the result.

In the presence of hCG, comparison of the chromogen-containing zones in the two detection portions permits a much more intense color to be observed in the determination portion than in the reference portion; a reverse result is observed in case of negative specimen.

EXAMPLE 2

Determination of antigens (hLH)

a) Preparation of cellulose-immobilized hLH—Determination and reference portions.

100 g of fiber cellulose is treated overnight, at room temperature, with a 30 U/ml solution of hLH in phosphate buffer, pH 7.2, the coated cellulose is washed with the same buffer and dried at 37° C. per 10 hours.

b) Preparation of peroxidase-labelled hLH—Determination and reference portions.

20 ml of anti-hLH ascites are precipitated 3 times by means of 18% anhydrous sodium sulfate, dissolved with 20 ml of distilled water subsequent to each precipitation, then dialyzed at +4° C. overnight against phosphate buffer, pH 7.2, 10 mM.

The dialyzed solution is treated with 200 mg of RZ 3.00 peroxidase and 50 mol of 25% glutaraldehyde at 4° C. for 48 hours. The solution is eluted on sodium chloride-equilibrated G-150 Sephadex, 50 mM. The eluted anti-hLH-peroxidase complex can be stored at −20° C.

c) Preparation of the labelled, support-adsorbed antibody—Determination and reference portions.

50 g of cellulose is treated with 5 ml of 1:300 diluted anti-hLH-peroxidase in phosphate buffer, 50 mM, pH 7.2, and dried at 37° C. overnight.

e) Preparation of the inert layer—Determination portion.

50 g of fibrous cellulose is treated at 37° C., overnight, with 1 l of phosphate solution, 0.1 M, pH 7.2, containing 3% bovine albumin and 0.5% bovine immunoglobulin. The saturated cellulose is washed 3 times with the same buffer then dried at 40° C. overnight.

f) Preparation of the polyclonal, irreversibly cellulose-adsorbed anti-hLH antibody—Reference portion.

50 g of fiber cellulose is treated at 37° C., overnight, with one liter of phosphate buffer, 0.1 M, pH 7.2, which contains previously purified, 1:300 diluted anti-hLH antibody. The coated cellulose is washed 3 times with phosphate buffer 0.1 M, ph 7.2, then dried at 40° C. overnight.

g) Preparation of the support-adsorbed chromogen—Determination and reference portions.

50 g of cellulose is treated with 50 mg of tetramethylbenzidine dissolved in 5 ml DMSO-water.

h) Packing of columns.

Two glasses columns (2 mm i.d., 15 cm long) are packed from bottom to top with the materials as follows: inert layer for the determination column; immobilized polyclonal anti-hLH antibody for the reference column; adsorbed peroxidase-anti-hLH for both columns; immobilized hLH for both columns; adsorbed chromogen for both columns, all prepared as above. The glass columns are closed up at both ends with cotton or suitable porous septa.

i) Carrying out the analysis.

Urine to be analyzed is brought into contact with the above described columns and rises in the columns by capillarity. When hLH is present in urine, hLH in the determination column will pass through the inert layer without any type of reaction being caused to occur, whereas hLH in the reference column will be retained by the cellulose-immobilized polyclonal antibody.

In the second zone of the determination column, hLH will bind to the anti-hLH-peroxidase and, in moving on up, it no longer produces any immunologic reaction with the immobilized hLH and continues to go up until reaching the chromogenic substrate in the last part of the column, which substrate will produce development of a blue color by reaction with the enzyme. In the reference column, the peroxidase-conjugated anti-hLH will bind to the immobilized hLH and be unabled to reach the chromogenic layer, except for a small fraction thereof which is unretained due to reaction equilibrium, and which causes a light coloration (background) to occur.

In case of negative urine, in both the determination and reference columns the rising peroxidase-conjugated anti-hLH will bind to the immobilized hLH and fail to reach the chromogen-containing layer, except a small fraction thereof which is unretained by the immobilized hLH due to equilibrium reaction, and which causes a light coloration (background) to occur.

l) Reading the result.

By comparing the developed colors in the two devices, it is observed that, in the presence of hLH, the chromogen-containing zone in the determination column shows to be much more intensely colored than that in the reference column; in case of absence of hLH, the result is reversed.

We claim:

1. A device for immunodiagnostic analysis of a component of a sample comprising:
   (a) a support divided into a determination portion and a reference portion in a first direction and into at least four regions in the following order in a direction perpendicular to said first direction;
   (b) a first region having in the reference portion only a component irreversibly fixed thereto which is immunocomplementary to the component being analyzed;
   (c) a second region having a component reversibly adsorbed thereto which is an enzyme-conjugated immunocomplement to the component being analyzed;
   (d) a third region having a component irreversibly fixed thereupon which is immunologically indistinguishable from the component being analyzed; and
   (e) a fourth region having fixed thereupon a substrate for said enzyme of the enzyme-conjugated immunocomplement of said second region, said substrate being convertible by said enzyme to produce a color change.

2. A device for immunodiagnostic analysis of a component of a sample comprising:
   (a) a support divided into a determination portion and a reference portion in a first direction and into at least four regions in the following order in a direction perpendicular to said first direction;
   (b) a first region containing no immunocomplementary components;
   (c) a second region having a component reversibly adsorbed thereto which is an enzyme-conjugated immunocomplement to the component being analyzed;
   (d) a third region having a component irreversibly fixed thereupon which is immunologically indistinguishable from the component being analyzed in said determination portion only, and having irreversibly fixed thereto a component immunocomplementary to the component being analyzed in said reference portion only; and (e) a fourth region having fixed thereupon a substrate for said enzyme of the enzyme-conjugated immunocomplement of said second region, said substrate convertible by said enzyme to produce a color change.

3. A device for immunodiagnostic analysis of an antibody component of a sample comprising:

(a) a support divided into a determination portion and a reference portion in a first direction and into at least four regions in the following order in a direction perpendicular to said first direction;

(b) a first region containing no immunocomplementary components;

(c) a second region having, in the determination portion, an enzyme-labelled antibody and in the reference portion an enzyme-labelled anti-antibody; analyzed;

(d) a third region having a component irreversibly fixed thereto which is an immobilized antigen; and (e) a fourth region having fixed thereupon a substrate for said enzyme of the enzyme-conjugated immunocomplement of said second region, said substrate being convertible by said enzyme to produce a color change.

4. A device for immunodiagnostic analysis of an antigen component of a sample comprising:

(a) a support divided into a determination portion and a reference portion in a first direction and into at least four regions in the following order in a direction perpendicular to said first direction;

(b) a first region containing no immunocomplementary components;

(c) a second region having, in the determination portion, antigens immunologically indistinguishable from the antigen component and, conjugated with an enzyme, reversibly absorbed thereupon, and in the reference portion, antibodies specific for the antigen component conjugated with an enzyme reversibly absorbed thereupon;

(d) a third region having irreversibly fixed thereupon antibodies specific for the antigen component; and (e) a fourth region having fixed thereupon a substrate for said enzyme of the enzyme-conjugated immunocomplement of said second region, said substrate convertible by said enzyme to produce a color change.

5. A device for immunodiagnostic analysis of an antibody component of a sample comprising:

(a) a support divided into a determination portion and a reference portion in a first direction and into at least four regions in the following order in a direction perpendicular to said first direction;

(b) a first region containing no immunocomplementary components;

(c) a second region having a component reversibly absorbed thereupon which is an enzyme-conjugated immunocomplement to the component being analyzed;

(d) a third region having, in the determination portion, an antibody component irreversibly fixed thereto which is indistinguishable from the antibody component being analyzed and, in the reference portion, an anti-antibody component irreversibly fixed thereto, which is reactive with said antibody component being analyzed; and (e) a fourth region having fixed thereupon a substrate for said enzyme of the enzyme-conjugated immunocomplement of said second region, said substrate convertible by said enzyme to produce a color change.

* * * * *